United States Patent [19]

McCabe et al.

[11] Patent Number: 5,098,715
[45] Date of Patent: Mar. 24, 1992

[54] FLAVORED FILM-COATED TABLET

[75] Inventors: Terrance T. McCabe, Durham; Robert A. Stagner; Joel E. Sutton, Jr., both of Greenville, N.C.

[73] Assignee: Burroughs Wellcome Co., Research Triangle Park, N.C.

[21] Appl. No.: 631,741

[22] Filed: Dec. 20, 1990

[51] Int. Cl.5 ............................................. A61K 9/36
[52] U.S. Cl. .................................... 424/479; 424/480; 426/96; 426/103; 427/2; 427/3
[58] Field of Search ................. 424/479, 480; 426/96, 426/103; 427/2, 3

[56] References Cited

U.S. PATENT DOCUMENTS

| | | | |
|---|---|---|---|
| 3,146,169 | 8/1964 | Stephenson | 167/82 |
| 3,256,111 | 6/1966 | Singiser | 117/85 |
| 3,786,159 | 1/1974 | Sato et al. | 426/96 X |
| 3,935,326 | 1/1976 | Groppenbacher | 427/3 |
| 4,154,636 | 5/1979 | Motoyama et al. | 156/243 X |
| 4,285,983 | 8/1981 | Saldarini et al. | 427/2 X |
| 4,302,440 | 11/1981 | John et al. | 424/480 X |
| 4,511,553 | 4/1985 | Boesig et al. | 427/3 X |
| 4,600,645 | 7/1986 | Ghebre-Sellassie et al. | 424/497 X |
| 4,753,790 | 6/1988 | Silva et al. | 426/103 X |

FOREIGN PATENT DOCUMENTS

| | | |
|---|---|---|
| 0058765 | 1/1982 | European Pat. Off. . |
| 2045749 | 10/1979 | Fed. Rep. of Germany . |
| 1273374 | 2/1962 | France . |
| 1396113 | 4/1975 | United Kingdom . |

Primary Examiner—Karl Group
Attorney, Agent, or Firm—Olive & Olive

[57] ABSTRACT

The invention comprises a flavored thin film coating on solid oral dosage pharmaceutical tablets containing unpleasant tasting ingredients such as triprolidine hydrochloride and pseudoephedrine hydrochloride. The flavored coating of the invention is comprised of a film-forming substance such as a hydroxypropyl methylcellulose and a polyethylene glycol, a sweetening agent and a flavoring agent. The method of the invention comprises aqueous spray-coating of the flavored sweetened coating onto the pharmaceutical tablets.

23 Claims, No Drawings

FLAVORED FILM-COATED TABLET

FIELD OF INVENTION

This invention relates to a thinly-coated pharmaceutical tablet and to methods of its preparation. In particular, the invention relates to a flavored, sweetened coated tablet.

BACKGROUND INFORMATION

Thin film coating of pharmaceutical tablets allows efficient, controlled, uniform and reproducible coats. Use of multiple layers of coating, such as the polymeric undercoat, polymeric pigmented second coat and polymeric finish coat allows the preparation of very smooth glossy tablets (Ohno, U.S. Pat. No. 4,001,390). This patent and all other cited patents are incorporated by reference herein.

Numerous methods for pan-coating pharmaceutical tablets have been developed and are summarized in *Pharmaceutical Dosage Forms: Tablets*, Volume 3 (eds. Lieberman and Lachman, 1982, Marcel Dekker). They include sugar-coating techniques, solvent film coating, aqueous film coating, delayed release coating, and granule coating. Pulverized medicine may also be wrapped in a transparent, glossy, resistant, soluble or semipermeable film as provided by Motoyama et al. (U.S. Pat. No. 4,154,636).

Pharmaceutical tablets have been coated for a variety of reasons, including masking objectionable flavors or odors, protecting unstable tablet compositions, providing protection of the tablet through the stomach with enteric coatings, improving the appearance of the tablet or separating medicine ingredients into a core segment and coating segment.

Aspirin tablets or other tablets that are powdery, easily dissolved and friable have been treated with a variety of coatings to keep them from dissolving too soon (John et al., U.S. Pat. No. 4,302,440). Also, other polymers in non-aqueous vehicles have been used to granulate tablets (Gans et al., U.S. Pat. No. 3,388,041) or to coat onto tablets (Jeffries, U.S. Pat. No. 3,149,040) to protect from dissolving in the stomach or to delay the drug's release. Other non-aqueous film-coating systems have been designed to be applied to a variety of tablets containing a variety of active ingredients as illustrated by Singiser, U.S. Pat. No. 3,256,111 and Brindamour, U.S. Pat. No. 3,383,236. The aqueous coating processes are environmentally more safe than the non-aqueous processes, which involve the use of organic solvents in film-coating solutions. Thin film coatings, which do not alter the dissolution characteristics of the tablet, may be readily formed using aqueous film-coating processes. Unless adequately thick or insoluble coatings are used, most coatings are not capable of effectively masking the strong objectionable bitter taste of triprolidine hydrochloride or other compounds with similar properties.

Previous attempts to solve the problem of masking the taste and odor of active ingredients in tablet form have led to slow-dissolving coatings, thicker coatings, and sugar coatings (sucrose or mannitol). Although an unflavored soluble film-coating may normally be adequately thick to effectively mask the objectionable bitter taste of triprolidine and other compounds with similar properties, persons who have difficulty swallowing such tablets may find that even tablets having adequately thick soluble film-coatings may partially dissolve in the mouth, thus decreasing the effectiveness of the coating in masking the objectionable flavor.

Tablets have been coated with compositions containing sugar or sugar substitutes to make them more palatable as well as to improve their appearance in some cases. One sugar-coating pan process involves applying a first water-repellent layer, a subcoat and a sugar coat, and coloring and polishing the sugar-coated tablet. The sugar-coating pan process is time-consuming and greatly increases the tablet size. It is believed that the prior sugar coatings do not include use of strong pleasant masking flavors to better disguise the bitter taste.

Although it is believed that strong, masking flavorings such as fruit or mint flavorings have not been used with tablet coatings, some flavorings have been used in liquid medicines. Liquid medicines having strong tastes have been mixed with sweet and/or flavored substances such as fruit flavors to mask the taste. For other oral, solid dosage forms, medicinal compounds have been mixed with waxy materials and water-swellable high molecular weight materials to mask objectionable tastes.

It is believed that the previous uses of flavorings or fragrances in thin-film coatings for pharmaceutical tablets have not utilized aqueous spray coatings and have included mild flavored or low concentrations of flavored ingredients having pronounced, characteristic fragrances for relatively mild-flavored medicines, especially those having an objectionable odor. Such flavored or fragrant coatings include a pressed film coating incorporating 0.5% orange essence to impart the smell of an orange (Motoyama, U.S. Pat. No. 4,154,636) and a non-aqueous air spray coating containing 5.2% ethyl vanillin on a vitamin tablet core (Singiser, U.S. Pat. No. 3,256,111). An aqueous film coating for aspirin in which unspecified flavorings were mentioned as optional additions is found in John, U.S. Pat. No. 4,302,440.

Another major function of tablet coatings has been to aid in tablet identification. Thus, the use of coatings containing pigments on tablets provides a way to identify tablets by color. Pigment addition also allows the tablets to have a more uniform and pleasing appearance. Tablet coatings comprising a colored film coating have been prepared, for example, by dispersing an anhydrous pigment suspension in a polymer solution (Signorino U.S. Pat. No. 3,981,984). However, persons with impaired vision often have difficulty in being sure that they are taking the correct medicine even with color-coded tablets.

OBJECTS OF THE INVENTION

This invention provides an unexpected advantage of masking unpleasant medicinal tastes such as that associated with triprolidine through the use of distinctive flavoring agents in combination with a sweetening agent in the aqueous coating dispersion. Thus, one object of this invention is to provide a thinly-coated pharmaceutical tablet wherein the unpleasant taste of the core tablet is masked by the flavored coating. Not only does the film coating of the invention hide an objectionable taste, but it also provides a perceptible pleasing taste to the tablet. This acceptable or pleasant taste component in the coating, in addition to the masking effect provided by the presence of the coating itself, is more effective than a coating by itself, in removing and covering unpleasant tastes. The flavored coating of the invention also provides a pleasant taste advantage even if the core tablet itself is neutral-tasting and does not have an objectionable taste.

Another object of the invention is to provide a coated pharmaceutical tablet that will enable oral identification of the tablet due to the particular flavor of the coat being associated with the particular core tablet composition. Oral flavor identification of this invention allows visually impaired as well as other persons to know that the correct medication is being taken so that mistakes in medication may be avoided.

Another object of the invention is to provide a coated pharmaceutical tablet that enables different strengths of the same active ingredient, such as a prescription medicine, to be identified by different flavored coatings being applied to the different ingredient strengths.

Another object of the invention is to provide a coated pharmaceutical tablet that enables increased compliance with prescribed medicine schedules. The flavored coat provides a flavored oral stimulus that enables those who have taken flavor-coated tablets to have an enhanced memory of having taken the tablet through remembrance of the particular flavor of coating. The flavored coating of the invention also enhances the appeal of a particular medicine so that persons do not avoid taking their medicine.

Another object of the invention is to provide a smooth easily swallowed tablet and to facilitate swallowing ease through increased salivation if the coated tablet lingers in the mouth and is tasted.

Another object of the invention is to provide a coated pharmaceutical tablet that does not slow the dissolution of the core tablet and in which the bioavailability of the active ingredients is not significantly reduced or impaired.

Another object of the invention is to provide a process for preparing a flavor-coated pharmaceutical tablet comprising an aqueous coating process, which is less hazardous to the environment than a non-aqueous coating process.

Another object of the invention is to provide a coated pharmaceutical tablet to reduce the potential for dust generation inherent in uncoated tablets.

Another object of the invention is to provide a flavor-coated pharmaceutical tablet in which the flavor is retained for the anticipated shelf life of the core tablet.

Still other objects and advantages of the invention will be apparent to those of skill in the art after reading the following description of the preferred embodiment.

SUMMARY OF THE INVENTION

The invention relates to a flavored thin film coating on solid oral dosage pharmaceuticals, in particular, those containing unpleasant-tasting active ingredients such as triprolidine hydrochloride. The method of the invention comprises applying a water-soluble, pharmaceutically-acceptable polymeric coating such as a hydroxypropyl methylcellulose coating containing a flavoring agent and a sweetening agent onto the exterior surfaces of the tablet.

DESCRIPTION OF THE PREFERRED EMBODIMENT

The method of this invention comprises standard pharmaceutical aqueous spray-coating techniques and conditions using a flavored coating. In particular, pharmaceutical core tablets are continuously (i.e., not intermittently) spray-coated with a thin film coating containing a flavoring agent and a sweetener. Suitably formulated core tablets are placed in a coating chamber. A preferred composition of coating material, of an excessive volume to allow coating losses to the pan, exhaust and spray equipment, is sprayed into the coating chamber until the coated tablets show a weight increase of 0.5 to 15.0 parts per 100 parts by weight of the core tablet weight. The preferred method of the invention comprises a one-step continuous spray-coating process to apply the thin flavored coating. Thus, the preferred embodiment is distinguishable from sugar-coating processes in which multiple layers of sugar-containing coating are applied, each followed by a drying period. It is also possible to apply more than one flavored coat or to apply the flavored coating after an initial sealing coat. If any coating, such as a wax coating, is applied after the flavored coating, it must be designed to allow taste perception of the flavored coating.

The preferred pharmaceutical tablet with which the flavored coating of this invention is used contains triprolidine hydrochloride and pseudoephedrine hydrochloride. These tablets contain from 12 to 300 mg pseudoephedrine hydrochloride per tablet and 0.5 to 12.5 mg triprolidine hydrochloride per tablet with the amounts of the active ingredients present in the tablets of the cited examples being 60 and 2.5 mg, respectively, in a typical 150 mg tablet. The coating increases the weight of the tablets by an average of 5%. Tablets containing either pseudoephedrine hydrochloride or triprolidine hydrochloride as the only active ingredient, also may be flavor-coated. The advantages of this invention are also realized through flavor-coating of other bitter or objectionably strong flavored tablets, especially those that bleed through the thin coating. Such other bitter or objectionable-tasting active ingredients include, but are not limited to, trimethoprim, sulfamethoxazole, guaifenesin, chlorpheniramine maleate, dextromethorphan, bupropion, azidothymidine and other salts or combinations of these ingredients and those of the preferred embodiment. The invention may also be used with sustained-release formulations.

The preferred film coating of this invention is comprised of a commercial film-coating product designed for aqueous film coating containing the water-soluble, film-forming resin, hydroxypropyl methylcellulose and polyethylene glycol (or other suitable plasticizing agents such as propylene glycol or glycerine) and optionally containing titanium dioxide (or other colorant or opacifying agent). Such a product is commercially available under the trade name Opadry White TM (Colorcon, West Point, Pa.). A suitable blend comprises 0 to about 20% w/w titanium dioxide or colorant, about 5 to about 95% w/w hydroxypropyl methylcellulose, and 0 to about 25% w/w polyethylene glycol. The most preferred embodiment comprises 10.5% non-water additives, of which 7.5% is Opadry. Therefore, most of the weight of the non-water additives of the coating dispersion is comprised of Opadry. More than 25% Opadry makes the coating too thick to spray easily while concentrations that are too low decrease the efficiency of coating. This blend plus flavoring and sweetening agents is added to purified water at ambient temperature in a vortex mixer such as a Lightnin Mixer Model V-7 (Mixing Equipment Co., Rochester, N.Y.). Other Opadry coating products such as Opadry Clear or Opadry with various pigment lakes may also be used in the invention to change the appearance of the tablets without adversely affecting the flavor characteristics of the invention. Other aqueous film-forming polymers may also be employed in place of hydroxypropyl methylcellulose.

Small amounts of a flavoring agent and a sweetening agent are added so that the total percent of the components added to the water is 2 to 25% w/w based on the weight of the total dispersion. Flavorings may be obtained from a variety of sources with the relevant criteria being strength and pleasing nature of the flavor. The flavor agent selected, the film coating dispersion formulation and the amount of solids sprayed on to the tablet affect the flavor strength of the desired product. The preferred flavoring amount is readily determined by balancing the goal of adding an amount sufficient to mask the core tablet taste and provide a distinct, characteristic and pleasing taste, and the goal of keeping the tablet from being too much like a candy or mint product. The desired strength of the flavoring may vary depending on the type of tablet and the intended recipients and the identity of the flavoring.

The sweetening agent in the preferred embodiment is confectioners sugar, but other sweetening agents such as saccharin, aspartame, mannitol, sorbitol or others used in foods, may also be employed. The preferred amount of sweetening agent will be a function of the sweetening capacity of the sweetening agent. For example, since aspartame is reported to be 160 times as sweet as sucrose, proportionally less aspartame than sucrose would be used to achieve the flavored, film-coated tablet of this invention. The preferred range of confectioners sugar is about 0.5 to about 10% based on the weight of the film coating. The more preferred range is 2.5 to 10%. Most preferred is 2.5%. Concentrations from about 2.5 to 10% sugar allow a thin coating of about 100 u thickness to be applied by the method of the invention to achieve the desired results of the invention.

The following equipment was used in practicing the method of this invention as demonstrated in the examples. The coating pan was an ACCELA-COTA ® (Thomas Engineering, Inc., Hoffman Estates, Ill.) having a 24-inch (60.96 cm) perforated coating pan rotating at about 8 rpm and providing about 1300 cu ft/min of inlet air at a temperature of 90° C. Tablet bed temperature was maintained at 45° C. Although 45° C. is the optimum temperature, acceptable quality coatings may be obtained at tablet temperatures from 38°-55° C. The spraying unit was an air-atomized Binks Model 460 spray gun with two guns per pan (Binks Manufacturing Co., Franklin Park, Ill.), operating at 50 psi hydraulic pressure. A Masterflex peristaltic pump (Cole-Parmer Instrument Co., Chicago, Ill.) with Model 7015 pumpheads and tubing was used to pump the dispersion formulation of the invention. Equipment to be used for scale-up operations would be obvious to a person skilled in the art of pharmaceutical coatings. For example, larger ACCELA-COTA pans of 48 or 60 inches would accommodate increased number of core tablets. It is also clear that the inlet air volume, rotation speed of the pan and temperature are interactive factors in coating operations and the cited parameters and equipment are for illustration purposes only and do not limit the invention. Although use of air spraying units results in more even coating of core tablets due to better droplet-size control, airless spraying units may also be utilized.

When the flavor-coated tablets as prepared by the method of this invention are administered to a recipient, the positive taste perception of the flavored coat of the invention lasts on the tongue for at least five seconds, which is generally more than enough time for the tablet to be swallowed before the tablet's bitterness becomes objectionable.

Because the flavors used in this invention are volatile, it would be expected that the high temperatures employed during manufacturing would cause the flavoring agents to volatilize during the spray-coating process and the flavors to be lost. The surprising and unexpected result in the actual practice of this invention is that when the flavoring agents are incorporated into the coating dispersion with a sweetener, the flavors are retained. In fact, the flavors continue to be retained strong for an unexpectedly long period. Core tablets containing triprolidine hydrochloride and pseudoephedrine hydrochloride coated with the method of the invention as exemplified in the examples below have been stored in blister packs at 30° C. for 24 months. Taste tests on these stored flavor-coated tablets revealed that the coating flavor is retained for at least 24 months, the anticipated shelf life for the coated tablets.

The following examples illustrate the invention without limiting it to the examples. In particular, numerous strongly flavored agents, such as other fruit flavors, other mint-related flavors and other natural and artificial flavors, may be employed in lieu of those in the examples.

EXAMPLE 1

A coating dispersion formulation of the following percentages (w/w) is prepared: Opadry White, 7.5; natural and artificial peppermint flavor (International Flavors and Fragrances, Inc., New York, N.Y.), 0.5; confectioners sugar, NF, 2.5; and purified water 89.5. Five (5) kg of core tablets, each containing the active ingredients, triprolidine hydrochloride (2.5 mg) and pseudoephedrine hydrochloride (60 mg) and a suitable binder, are placed in a 24-inch ACCELA-COTA rotating at 8 rpm. A coating dispersion is applied using an air-atomized sprayer and standard coating procedures. Tablets with this coating possess a pleasant peppermint flavor when tasted.

The dissolution results of individual tablets using the USP/Paddle method (50 rpm in 900 ml distilled water at 37° C.) are shown in Table 1. The table shows the mean percent of the core tablet active ingredients dissolved over time for coated and uncoated tablets (lower half of table as compared to upper half of table) as well as the standard deviation (SD) and the relative standard deviation (RSD). The coating did not impair dissolution of the tablet.

TABLE 1

| | PERCENT COMPOUND DISSOLVED (Uncoated Tablets) | | | | | |
|---|---|---|---|---|---|---|
| | Pseudoephedrine HCl | | | Triprolidine HCl | | |
| Tablet | 15 min | 30 min | 45 min | 15 min | 30 min | 45 min |
| 1 | 97.8 | 98.2 | 98.0 | 94.1 | 96.2 | 96.5 |
| 2 | 96.7 | 96.5 | 96.4 | 90.7 | 91.6 | 93.1 |
| 3 | 99.1 | 99.0 | 99.5 | 92.3 | 93.0 | 95.2 |
| 4 | 94.4 | 97.6 | 98.8 | 88.8 | 92.9 | 93.5 |
| 5 | 100.5 | 100.2 | 101.3 | 90.1 | 92.6 | 91.6 |
| 6 | 91.7 | 95.9 | 98.2 | 83.5 | 92.2 | 94.5 |
| Mean | 96.7 | 97.9 | 98.7 | 89.9 | 93.1 | 94.1 |
| SD | 3.2 | 1.6 | 1.6 | 3.6 | 1.6 | 1.7 |
| % RSD | 3.3 | 1.6 | 1.7 | 4.0 | 1.7 | 1.8 |
| | PERCENT COMPOUND DISSOLVED (Coated Tablets) | | | | | |
| 1 | 98.1 | 99.5 | 97.9 | 92.2 | 92.8 | 91.0 |
| 2 | 97.1 | 99.3 | 99.2 | 91.4 | 92.3 | 93.1 |
| 3 | 94.9 | 95.2 | 96.3 | 90.0 | 88.9 | 91.7 |
| 4 | 95.6 | 97.2 | 97.6 | 91.6 | 95.1 | 93.6 |
| 5 | 93.2 | 92.6 | 94.3 | 88.5 | 94.6 | 89.4 |

TABLE 1-continued

| | PERCENT COMPOUND DISSOLVED (Uncoated Tablets) | | | | | |
|---|---|---|---|---|---|---|
| | Pseudoephedrine HCl | | | Triprolidine HCl | | |
| Tablet | 15 min | 30 min | 45 min | 15 min | 30 min | 45 min |
| 6 | 99.6 | 99.3 | 100.1 | 94.2 | 97.6 | 93.2 |
| Mean | 96.4 | 97.2 | 97.6 | 91.3 | 93.6 | 92.0 |
| SD | 2.3 | 2.8 | 2.1 | 2.0 | 3.0 | 1.6 |
| % RSD | 2.4 | 2.9 | 2.1 | 2.1 | 3.2 | 1.8 |

EXAMPLE 2

A coating dispersion formulation of the following percentages (w/w) is prepared: Opadry White, 7.5; natural and artificial peppermint flavor, 2.0; confectioners sugar, NF, 10.0; and purified water, 80.5. Five (5) kg of core tablets, each containing the active ingredients, triprolidine hydrochloride (2.5 mg) and pseudoephedrine hydrochloride (60 mg) and a suitable binder, are placed in a 24-inch ACCELA-COTA rotating at 8 rpm. A coating dispersion is applied using an air-atomized sprayer and standard coating procedures. Tablets with this coating possess a pleasant peppermint flavor when tasted.

Dissolution results of individual tablets using the USP/Paddle method at 50 rpm in 900 ml distilled water tablets at 37° C. are shown in Table 2.

TABLE 2

| | PERCENT COMPOUND DISSOLVED (Uncoated Tablets) | | | | | |
|---|---|---|---|---|---|---|
| | Pseudoephedrine HCl | | | Triprolidine HCl | | |
| Tablet | 15 min | 30 min | 45 min | 15 min | 30 min | 45 min |
| 1 | 103.7 | 104.0 | 103.7 | 102.8 | 103.8 | 106.8 |
| 2 | 96.0 | 97.0 | 97.5 | 99.3 | 97.2 | 100.2 |
| 3 | 98.9 | 99.7 | 98.6 | 99.0 | 101.0 | 99.7 |
| 4 | 99.5 | 99.4 | 99.7 | 99.8 | 100.7 | 100.0 |
| 5 | 100.8 | 101.4 | 101.1 | 97.0 | 98.4 | 98.1 |
| 6 | 105.9 | 105.4 | 106.1 | 101.0 | 96.6 | 101.5 |
| Mean | 100.8 | 101.2 | 101.1 | 99.9 | 99.6 | 101.1 |
| SD | 3.5 | 3.1 | 3.3 | 1.9 | 2.7 | 3.0 |
| % RSD | 3.5 | 3.1 | 3.2 | 1.9 | 2.7 | 3.0 |
| | PERCENT COMPOUND DISSOLVED (Coated Tablets) | | | | | |
| 1 | 99.7 | 103.2 | 101.5 | 96.3 | 99.6 | 106.3 |
| 2 | 104.1 | 104.6 | 103.8 | 97.8 | 96.8 | 101.1 |
| 3 | 97.3 | 97.5 | 95.6 | 95.8 | 92.1 | 98.9 |
| 4 | 104.4 | 103.9 | 103.0 | 98.8 | 96.9 | 98.6 |
| 5 | 99.3 | 100.5 | 99.0 | 92.4 | 95.8 | 97.1 |
| 6 | 103.5 | 103.0 | 103.1 | 97.9 | 97.1 | 96.2 |
| Mean | 101.4 | 102.1 | 101.0 | 97.3 | 97.2 | 99.7 |
| SD | 3.0 | 2.7 | 3.2 | 1.1 | 1.3 | 3.6 |
| % RSD | 2.9 | 2.6 | 3.1 | 1.1 | 1.3 | 3.7 |

EXAMPLE 3

A coating dispersion formulation of the following percentages (w/w) is prepared: Opadry White, 7.5; natural and artificial cherry marasque flavor, 2.0; confectioners sugar, NF, 10.0; and purified water, 80.5. Five (5) kg of core tablets, each containing the active ingredients, triprolidine hydrochloride (2.5 mg) and pseudoephedrine hydrochloride (60 mg) and a suitable binder, are placed in a 24-inch ACCELA-COTA rotating at 8 rpm. A coating dispersion is applied using an air-atomized sprayer and standard coating procedures. Tablets with this coating possess a pleasant cherry flavor when tasted.

EXAMPLE 4

A coating dispersion formulation of the following percentages (w/w) is prepared: Opadry Clear, 7.5; natural and artificial peppermint flavor, 2.0; confectioners sugar, NF, 10.0; and purified water, 80.5. Five (5) kg of core tablets, each containing the active ingredients, triprolidine hydrochloride (2.5 mg) and pseudoephedrine hydrochloride (60 mg) and a suitable binder, are placed in a 24-inch ACCELA-COTA rotating at 8 rpm. A coating dispersion is applied using an air-atomized sprayer using coating procedures that are standard. Tablets with this coating possess a pleasant peppermint flavor when tasted.

We claim:

1. A pharmaceutical tablet comprising an unpleasant tasting, solid core and a flavored, pharmaceutically acceptable, thin film coating, said coating increasing the weight of the tablet by an average of about 5%, said coating comprising a water-soluble, film-forming polymer, a volatile flavoring agent and a sweetening agent, said coating being capable of masking the unpleasant taste of the core, and said coating having a flavor that is retained in the coating for at least about 24 months during storage and that provides a taste perception of said flavor for at least five seconds after oral administration of said tablet.

2. The pharmaceutical tablet of claim 1, wherein the core comprises triprolidine hydrochloride and pseudoephedrine hydrochloride.

3. The pharmaceutical tablet of claim 2, wherein the pharmaceutically acceptable, polymeric coating comprises hydroxypropyl methylcellulose and a plasticizing agent, the flavoring agent comprises peppermint flavoring and the sweetening agent comprises confectioners sugar.

4. The pharmaceutical tablet of claim 3, wherein the pharmaceutically acceptable, polymeric coating further contains titanium dioxide.

5. The pharmaceutical tablet of claim 2, wherein the pharmaceutically acceptable, polymeric coating comprises hydroxypropyl methylcellulose and a plasticizing agent, the flavoring agent comprises fruit flavoring and the sweetening agent comprises confectioners sugar.

6. The pharmaceutical tablet of claim 5, wherein the pharmaceutically acceptable, polymeric coating further contains titanium dioxide.

7. The pharmaceutical tablet of claim 1, wherein the core comprises triprolidine hydrochloride.

8. The pharmaceutical tablet of claim 1, wherein the core comprises pseudoephedrine hydrochloride.

9. A pharmaceutical tablet according to claim 1, wherein the film coating comprises hydroxypropyl methylcellulose.

10. A pharmaceutical tablet according to claim 9, wherein the sweetening agent comprises sucrose.

11. A pharmaceutical tablet according to claim 10, wherein the sweetening agent comprises confectioners sugar.

12. A pharmaceutical tablet according to claim 11, wherein the sweetening agent comprises about 2.5 per cent based on the weight of the film coating.

13. A pharmaceutical tablet according to claim 1, wherein the sweetening agent comprises about 2.5 per cent based on the weight of the film coating.

14. A method for preparing flavor-coated pharmaceutical tablets, comprising the steps of:
   (a) preparing an aqueous dispersion comprising a pharmaceutically acceptable, film-forming substance, a volatile flavoring agent and sweetening agent, said film-forming substance comprising a water-soluble polymer;

(b) placing unpleasant tasting uncoated core tablets in a coating pan; and (c) spray-coating the aqueous dispersion onto the exterior surface of the core tablets at a pan rotation speed and under air flow and temperature conditions sufficient to enable evaporation of water and even-coating of the core tablets, said conditions sufficient to provide a flavored coating that increases the weight of the tablet by an average of about 5%, said flavored coating being capable of masking the unpleasant taste of the core, and said flavored coating having a flavor that is retained in the coating for at least about 24 months during storage and that provides a taste perception of said flavor for at least five seconds after oral administration of said tablet.

15. The method of claim 14, wherein the pan is perforated and is rotated at about 8 rpm, the inlet airflow rate is about 1300 cubic feet per minute, the air temperature is about 90 degrees C., and the bed temperature is about 45 degrees C.

16. The method of claim 14, wherein:
(a) the pharmaceutically acceptable, polymeric, film-forming substance comprises hydroxypropyl methylcellulose, titanium dioxide and polyethylene glycol; and
(b) the aqueous dispersion is comprised of about 7.5% pharmaceutically acceptable, polymeric, film-forming substance, about 0.5% flavoring agent, and about 2.5% sweetening agent.

17. The method of claim 16, wherein the flavoring agent is peppermint flavoring.

18. The method of claim 16, wherein the flavoring agent is fruit flavoring.

19. The method of claim 14, wherein said core tablets comprise triprolidine hydrochloride and pseudoephedrine hydrochloride.

20. A method of claim 14, wherein the sweetening agent comprises sucrose.

21. A method according to claim 20, wherein the sweetening agent comprises confectioners sugar.

22. A method according to claim 14, wherein the film-forming substance comprises hydroxypropyl methylcellulose.

23. A pharmaceutical tablet comprising an unpleasant tasting, solid core and a flavored, pharmaceutically acceptable, thin film coating, wherein said coating has been formed by application of an aqueous dispersion of a water-soluble, polymeric film-forming substance, said coating increasing the weight of the tablet by an average of about 5%, said coating comprising a volatile flavoring agent and a sweetening agent, said coating being capable of masking the unpleasant taste of the core, and said coating having a flavor that is retained in the coating for at least about 24 months during storage and that provides a taste perception of said flavor for at least five seconds after oral administration of said tablet.

* * * * *